United States Patent

Schulsinger et al.

[11] Patent Number: 5,897,572
[45] Date of Patent: Apr. 27, 1999

[54] MICROSURGICAL SUTURE NEEDLE

[75] Inventors: David A. Schulsinger, New York; Philip S. Li, Flushing; Marc Goldstein, New York, all of N.Y.

[73] Assignee: Cornell Research Foundation, Inc., Ithaca, N.Y.

[21] Appl. No.: 08/940,960

[22] Filed: Oct. 8, 1997

Related U.S. Application Data

[XX .
[60] Provisional application No. 60/027,910, Oct. 11, 1996.

[51] Int. Cl.⁶ .................................................... A61B 17/04
[52] U.S. Cl. ............................ 606/224; 606/222; 606/223
[58] Field of Search .................................... 606/222, 223, 606/224

[56]       References Cited

U.S. PATENT DOCUMENTS

| 2,841,150 | 7/1958 | Riall . |
| 2,869,550 | 1/1959 | Kurtz . |
| 3,038,475 | 6/1962 | Orcutt . |
| 3,394,704 | 7/1968 | Dery . |
| 4,524,771 | 6/1985 | McGregor et al. . |
| 4,660,559 | 4/1987 | McGregor et al. ...................... 606/222 |
| 4,777,096 | 10/1988 | Borysko ................................... 428/571 |
| 4,932,961 | 6/1990 | Wong et al. ............................. 606/223 |
| 5,030,228 | 7/1991 | Wong et al. ............................. 606/223 |
| 5,041,127 | 8/1991 | Troutman ................................. 606/223 |
| 5,330,441 | 7/1994 | Prasad et al. ........................... 606/222 |
| 5,403,344 | 4/1995 | Allen ....................................... 606/223 |
| 5,464,422 | 11/1995 | Silverman ............................... 606/223 |

*Primary Examiner*—Gary Jackson
*Attorney, Agent, or Firm*—Jones, Tullar & Cooper, P.C.

[57]       ABSTRACT

The invention is directed to a microsurgical needle for use in microsurgical techniques. The distal segment of the needle is straight with a circular cross section, and has a sharpened tip with a triangular cross section having three sharp edges for cutting rather than tearing tissue during penetration. The middle segment of the needle has an acutely angled arched shape, and a transitional cross section which transitions between a squared cross section of the main shaft segment and the circular cross section of the straight distal segment. The main shaft segment of the needle has a generally squared cross section, and forms a broadly curved or arched shaft segment which may be easily gripped by a needle holder. The proximal end of the needle forms a suture attachment segment, and may be circular in cross section. The shape of the needle provides an easy angle, better stability, superior tissue alignment, and better control than conventional. needles, while the point is designed to minimize tissue trauma.

20 Claims, 2 Drawing Sheets

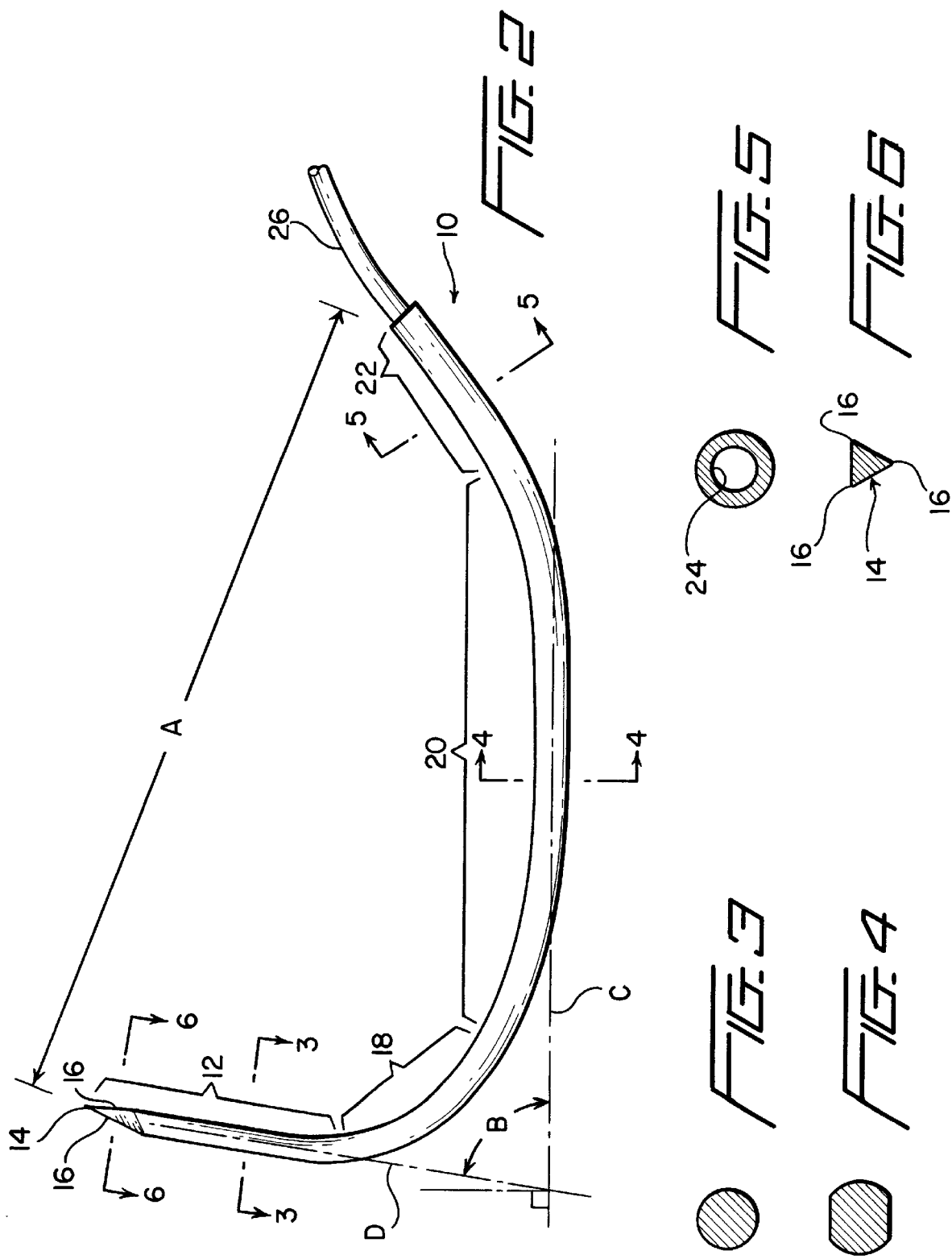

MICROSURGICAL SUTURE NEEDLE

CROSS-REFERENCE TO RELATED APPLICATION

This is a continuation-in-part of S.N. 60/027,910, filed on Oct. 11, 1996.

FIELD OF THE INVENTION

This invention is directed to a needle for use in forming sutures in tissue. In particular, this invention is directed to a microsurgical needle which is specially shaped so as to increase the degree of control and ease of use for the surgeon, while also reducing tissue trauma.

DESCRIPTION OF THE PRIOR ART

Surgical needles for applying sutures to living tissue are well known in the art. Typically the sutures are used to close wounds or adjoin adjacent tissue. Suturing needles are usually made from a cut blank or a length of wire of a material such as stainless steel. The blank is then shaped using well known machining techniques to form the surgical needle.

Surgical needles may be of a variety of shapes ranging from straight to curved. Curved needles are essential to most surgical procedures involving delicate or fine tissue to accurately locate the suture loop with respect to the tissue for minimizing trauma. Curved needles usually include a shaft portion, a proximal end portion for receiving a swaged suture thread, and distal tip portion which is generally sharpened for puncturing tissue. Some needle tips also include cutting edges which increase the sharpness of the tip, thereby reducing the amount of force required to insert the needle into tissue. An additional advantage of the cutting edges on the tip is reduced trauma to the tissue being penetrated, as the cutting edges create a cleaner incision, with less tearing of the tissue.

To insert a curved needle into tissue, a surgeon must grasp the shaft of the needle with a needle holder, generally near the center of the needle, or near its proximal end. The tip of the needle may then be inserted into the tissue near the edge of the tissue. The curvature of the needle helps establish the degree of control that the surgeon has over the movement of the needle tip through the tissue. The stability of the needle holder in grasping the needle shaft also plays an important role in the degree of control which the surgeon is able to exercise while forming the sutures.

In microsurgery, the suture needles are of extremely small size. Unlike in standard gross-field sutures, where the suture material is in the range of 24 gauge to 6–0 material, and may be swaged or threaded to needles of significantly larger diameter, microsurgery requires the use of suture material in the range of 80 (0.04 mm) to 11–0 (0.019 mm) in diameter, typically swaged to needles of 0.05 to 0.15 mm in diameter. With needles of such small diameter, the parameters discussed above, such as stability, strength, and control become of even greater importance.

The subject invention provides significant advances over conventional microsurgical suturing needles. The subject invention provides increased stability and control when compared with conventional needles, while simultaneously reducing the trauma to the tissue being penetrated.

SUMMARY OF THE INVENTION

The invention is directed to a microsurgical needle for use in microsurgical techniques. The needle has four specific segments: (1) a distal segment of the needle is straight with a circular cross section, and has a tip with a triangular cross section having three sharp edges for cutting rather than tearing tissue during penetration; (2) a middle segment of the needle has an acutely angled arched shape, and a transitional cross section which transitions between a squared cross section of a main shaft segment and the circular cross section of the straight distal segment; (3) a main shaft segment of the needle is generally squared in cross section, and forms a broadly curved or arched shaft segment which may be easily gripped by a conventional needle holder; and (4) the proximal end of the needle forms a suture attachment segment, and. is preferably circular in cross section. The shape of the needle provides an easy angle, better stability, improved point placement, and better control than conventional needles, while the point serves to minimize tissue trauma.

BRIEF DESCRIPTION OF THE DRAWINGS

FIG. 2 is a side elevation view of the needle of FIG. 1.

FIG. 3 is a cross section view taken along line 3—3 of FIG. 2.

FIG. 4 is a cross section view taken along line 4—4 of FIG. 2.

FIG. 5 is a cross section view taken along line 5—5 of FIG. 2.

FIG. 6 is a cross section view taken along line 6—6 of FIG. 2.

DESCRIPTION OF THE PREFERRED EMBODIMENT

Figure 1:
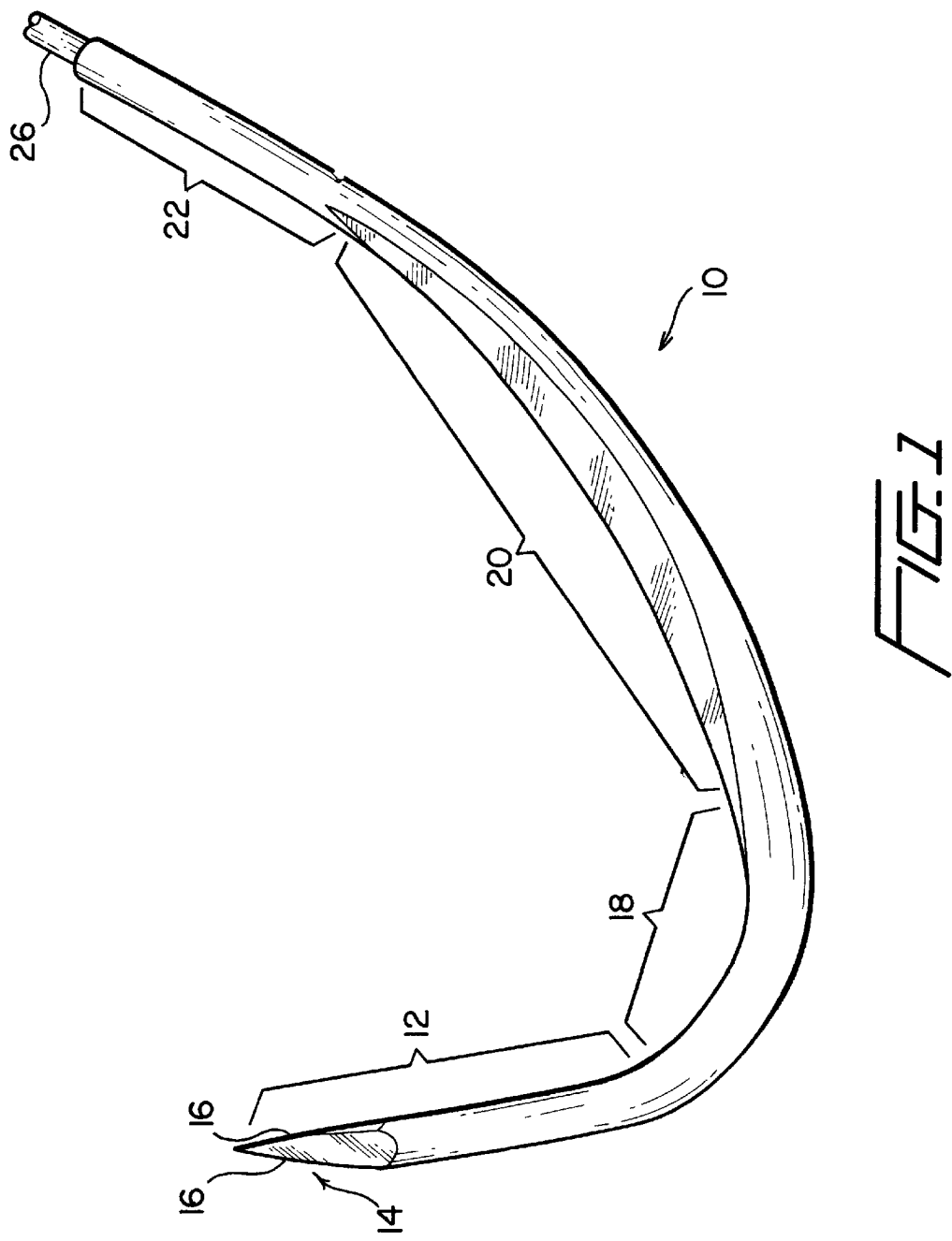
FIG. 1 is a perspective view of the microsurgical suture needle of the present invention.

The invention is directed to a microsurgical needle for use in forming sutures in living tissue or the like. Referring to FIGS. 1 and 2, needle 10 includes four specific segments. A straight distal segment 12 of the needle is generally straight when viewed in side elevation, and has a generally circular cross section, as shown in FIG. 3. Straight segment 12 terminates distally in a tip 14 having a triangular cross section, as shown in FIG. 6. It may be noted that straight segment 12 extends proximally of tip 14 for a significant distance with respect to the overall length A of needle 10. In one preferred embodiment, the overall length A of needle 10 is 7.5 mm from distal tip to proximal end, and the length of segment 12 is 2.5 mm. However, the length of segment 12 may vary depending on the designated application for needle 10, and it is desirable that segment 10 be at least as long as the thickness of at least one of the tissue layers being penetrated. Thus, segment 12 would generally extend between 1.0 and 3.5 mm beyond tip 14. This makes straight segment 12 between 15 and 45 percent of the overall length A of needle 10, and about 33 percent of the overall length of needle 10 in the preferred embodiment.

Figure 7:
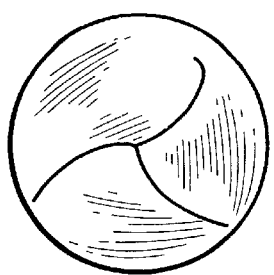
FIG. 7 shows a representation of a hole made in tissue by a needle having the non-traumatic tip of the present invention.
Figure 8:
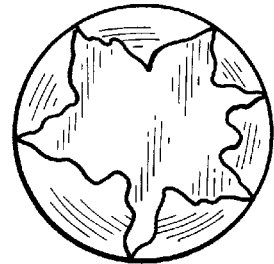
FIG. 8 shows a representation of a hole made in tissue by a prior art needle having a conventional tip configuration.

Tip 14 provides needle 10 with three sharp cutting edges 16. One cutting edge 16 faces outward along the major radius of needle 10, while the other two cutting edges 16 are transverse to the major radius of needle 10. As illustrated by FIG. 7, these sharp cutting edges 16 serve to form an incision-like opening in tissue during penetration, rather than tearing tissue, as is the case with conventional needles, as illustrated by FIG. 8. This cutting action is advantageous since less trauma is effected as the needle passes through the tissue, thus ensuring less damage and quicker healing. One preferred form which the non-traumatic tip 14 of the present invention may take is that of the SHARPOINT® micro-edge taper needle (M.E.T.®) tip which is marketed by Surgical Specialties Corporation, P.O. Box 310, Reading, Pennsylvania, 19607.

An acutely curved middle shaft segment 18 of needle 10 has an acutely-angled arched shape, and a transitional cross section which transitions between a squared cross section of a main shaft segment 20 and the round cross section of straight segment 12. As illustrated in FIG. 2, because of the curve formed by segment 18, an angle B between the centerline D of segment 12 and the tangentline C of main shaft segment 20 is less than 90 degrees in the preferred embodiment. The tangentline C of main shaft segment 20 is the line generally tangential to the radius of curvature of main shaft segment 20 at its centerpoint, and is tangential to main, segment 20 at the approximate location where a conventional needle holder would be used to grip needle 10. Angle B may generally be between 60 and 100 degrees, but is preferably between 80 and 90 degrees for enabling easy placement of tip 14 by a surgeon when needle 10 is being grasped by a needle holder. The acute angle B formed by segment 18 also provides a desirable turn-around action as the needle is passed through tissue.

Main shaft segment 20 of the needle is generally squared on top and bottom, when viewed in cross section, as shown in FIG. 4. When viewed in side elevation, main shaft segment 20 has a broadly curved or arched shape, and is approximately 5 mm long in the preferred embodiment, but this dimension may be varied according to a desired use. Main shaft segment 20 connects proximally to a suture attachment segment 22, which, as illustrated in FIG. 5, may be rounded in cross section for swaged attachment of a suture, as is known in the art.

The design of the surgical needle 10 of the present invention contributes to its strength, its ease of control, and its ability to easily pierce the tissue being sutured accurately and with minimal trauma to that tissue. It may be seen that due to the relative acuteness of middle shaft segment 18, main shaft segment 20 forms an angle B which is generally a right angle with respect to straight segment 12. This enables precise placement of tip 14 when needle 10 is being held by a conventional needle holder. In addition, since main shaft segment 20 is broadly arched, main shaft. segment 20 may be gripped at various locations along a substantial portion of its length while only mildly affecting the attitude of straight segment 12 with respect to a needle holder. Moreover, the squared cross section of main shaft segment 20 enables a needle holder to securely grip main shaft segment 20 with minimal clamping force, further contributing to the increased control achieved by the present invention, while reducing the tendency of the needle holder to flatten out the broad curve of main shaft segment 20.

In another important aspect of the invention, the straight configuration of straight segment 12 provides the advantage of enabling two adjacent layers of tissue to be pierced more precisely than is the case with conventional needles. It may be seen that as tip 14 is inserted into tissue, the straightness of straight segment 12 causes the penetration to occur in a straight line, rather than on a curve as in conventional needles. The curved. portions of the needle proximal to straight segment 12 then enable the surgeon to pass the remainder of the needle through the tissue layers in a convention manner. Thus, straight segment 12 enables a surgeon to more precisely align the tissue being sutured, a. feature which is particularly valuable in the case of microsurgery, where precise positioning of adjacent layers of tissue iE essential.

The needle of the present invention may be manufactured using any of the methods well known in the art of needle making. The needle is preferably constructed from a 300 series stainless steel, but other suitable materials may also be used. The shown preferred embodiment is of stainless steel wire 140 microns in diameter at the cross section shown in FIG. 5.

Proximal suture attachment segment 22 of needle 10 includes an axial hole 24 for receiving and securing a suturing thread 26 by swaging or the like. Of course other means, such as a crimping channel, may alternatively be used for securing suturing thread 26 to suture attachment segment 22.

Any absorbable or non-absorbable standard suture material may be used with the disclosed needle 10. The preferred suture thread for use with needle 10 is a 9–0 vicryl suture manufactured by ETHICON, INC. of Somerville, New Jersey, although any alternative suitable suture materials and diameters may also be used.

One particular use for needle 10 of the present invention is in the suturing of graft tissue during the treatment of hypospadias. Hypospadias is a well recognized urologic congenital anomaly, occurring in 1 of 300 newborn boys in which the urethral opening is at a point proximal to the end of the penis. In most instances, primary reconstruction can be accomplished with local penile and preputial skin. Occasionally, the pediatric urologist is confronted with the situation of deficient genital skin due to a prior operation or a high degree of urethral abnormality. In such instances, free extragenital non-hair-bearing skin tissue, bladder mucosa tissue, and buccal mucosa tissue have been used as; grafts for forming a urethra. The graft tissue is implanted into the penis to form a complete urethra.

The present needle is useful in a two-step microsurgical procedure to repair the hypospadias. A flat piece of graft tissue is first formed into a tubular configuration, and the tubular graft is then implanted as a urethral implant. Microsurgery is advantageous because it avoids large needle trauma, allows more precise apposition of tissue, and identifies exact needle placement to tissue. The needle of the present invention is useful for suturing the edges of the graft tissue together during tubularization of the graft tissue, and for implanting the graft, as described in Provisional Patent Application Ser. No. 60/027,915 and in the corresponding non-provisional patent application filed concurrently herewith (CRF D-1972A) of the inventors herein entitled "Method and Apparatus for Support and Tubularization of Surgical Grafts", and Provisional Patent Application Serial No. 60/027,935 and in the corresponding nonprovisional patent application filed concurrently herewith (Attorney Docket No. CRF D-1971A), by the inventors herein, entitled "Preserving Tissue", the disclosures of which are incorporated herein by reference.

Needle 10 is gripped along main shaft segment 20 using a conventional needle holder. When so gripped, straight segment 12 is almost at a right angle to main shaft segment 20 due to the relative acuteness of middle shaft segment 18. This enables precise placement of tip 14 by the surgeon. As tip 14 is inserted into the tissue, the sharp edges will cleanly incise the tissue, rather than stretch and tear the tissue. The incisions formed by tip 14 cause less trauma to the tissue than the prior art, and are believed to promote quicker healing of the sutured areas.

In addition, when penetrating tissue, since segment 12 is straight, it is easier for the surgeon to determine where tip 14 will penetrate adjacent tissue layers. Needle 10 will pass straight through the tissue in the direction of push, unlike curved needles in which the curve of the needle near the tip will cause a sideways movement of the tip through the tissue. During microsurgery precise point placement can be highly important to the success of the operation. Thus, when suturing two tissue layers together, it is desirable that straight segment 12 be of a length at least sufficient for tip 14 to completely penetrate the first layer of tissue, and preferably also the second layer of tissue prior to the entry of segment 18 into the first layer of tissue. This enables precise alignment of the tissues being sutured.

Once segment 12 has penetrated the tissue layers being sutured in the locations desired, acutely curved segment 18 will enter the tissue and provide a desirable turn-around of needle 10 as segment. 18 passes through the tissue. A portion of main segment 20 may also be inserted into the tissue at this point. The grip of the needle holder is then released, and the needle is gripped from the opposite side of the tissue and drawn the rest of the way through, thereby also drawing the suture material through the tissue.

Thus, it may be seen that in an operation such as microsurgical repair of hypospadias, needle 10 of the present invention reduces the trauma to the graft tissue, and enables the precise placement of sutures. The straight segment 12 of needle 10 is particularly advantageous in the precise alignment of adjacent tissue layers. It should be kept in mind, however, that the present invention may be used for forming sutures whenever microsurgical techniques are required, and that the invention is by no means limited only to use for hypospadias repair.

Although preferred embodiments of the invention have been described herein in specifics, the use of those specifics is not intended to limit the invention in any way. It will be recognized. that a variety of changes may be made, and equivalent structures adopted, without departing from the spirit of the invention that is intended to be covered by this patent.

What is claimed is:

1. A needle for use in forming sutures in tissue during microsurgery, said needle comprising:
   a first segment having a distal tip, said first segment extending proximally in a generally straight line substantially beyond said tip;
   a second segment contiguous to said first segment and extending proximally therefrom, said second segment forming an acute angle between said first segment and a third segment, said third segment being broadly curved relative to said second segment for enabling gripping of said needle by a needle holder.

2. The needle of claim 1 further including a fourth segment for attaching a suture thread to said third segment at the proximal end of said third segment.

3. The needle of claim 1 in which said third segment has a generally squared top and bottom in cross section to further facilitate gripping of said needle by a needle holder.

4. The needle of claim 1 in which said tip is triangular with three cutting edges for cutting tissue during penetration.

5. The needle of claim 1 in which the length of said first segment is greater than the thickness of the tissue to be penetrated such that said tip completely penetrates the tissue before said second segment begins to enter the tissue.

6. The needle of claim 1 in which the length of said first segment is between 1.0 and 3.5 mm, and the overall length of the needle is approximately 7.5 mm.

7. The needle of claim 1 in which the length of said first segment is approximately 33 percent of the overall length of said needle.

8. A needle for suturing two adjacent layers of tissue to each other, said needle comprising:
   a generally straight segment having a tissue-penetrating tip formed on its distal end, said straight segment being of a length greater than the thickness of a least one of the tissue layers;
   a second segment formed contiguously with the proximal end of said first segment, said second segment connecting said first segment to a broadly curved third segment, said second segment being curved so that said first segment extends generally at a right angle to a line tangential to the curve at the center of said third segment.

9. The needle of claim 8 further including a fourth segment for attaching a suture thread to said third segment at the proximal end of said third segment.

10. The needle of claim 8 in which said third segment has a generally squared top and bottom in cross section to further facilitate gripping of said needle by a needle holder.

11. The needle of claim 8 in which said tip is triangular with three cutting edges for cutting tissue during penetration.

12. The needle of claim 8 in which the length of said first segment is greater than the thickness of the tissue to be penetrated such that said tip completely penetrates the tissue before said second segment begins to enter the tissue.

13. The needle of claim 8 in which the length of said first segment is between 1.0 and 3.5 mm.

14. The needle of claim 8 in which the length of said first segment is approximately 33 percent of the overall length of said needle.

15. A needle for forming sutures in layers of adjacent tissue, said needle comprising:
   a generally straight first segment, said first segment having an non-traumatic tip formed on its distal end comprising a triangular shape with three cutting edges for cutting tissue during penetration by said tip; and
   a curved second segment proximal of said first segment, said second segment having a curvature whereby the centerline of said first segment is generally at a right angle relative to a line tangential to the center of the radius of curvature of a third segment, said third segment being proximal of said first and second segments.

16. The needle of claim 15 in which said generally right angle is between 100 and 80 degrees.

17. The needle of claim 15 further including a fourth segment for attaching a suture thread proximally of said third segment.

18. The needle of claim 15 in which the length of said first straight segment is between 1.0 and 3.5 mm.

19. The needle of claim 15 in which said first segment is of sufficient length to enable tip 14 to completely penetrate a layer of tissue prior to entry of said second segment into the tissue.

20. The needle of claim 15 in which the length of said first segment is approximately 33 percent of the overall length of said needle.

* * * * *